United States Patent [19]

Allen et al.

[11] 4,187,836
[45] Feb. 12, 1980

[54] FLOATING PISTON RESPIRATING PUMP

[75] Inventors: Richard T. Allen, Easton, Md.; Rudolph H. Moyer, West Covina, Calif.; Donald J. Sibbett, Cucamonga, Calif.; Howard H. Anderson, Covina, Calif.; Glen R. Martner, Rosemead, Calif.; Don Willis, Garden Grove, Calif.

[73] Assignee: Geomet, Inc., Gaithersburg, Md.

[21] Appl. No.: 901,653

[22] Filed: May 1, 1978

[51] Int. Cl.² .......................... G01N 1/22; A61B 5/02
[52] U.S. Cl. ........................ 128/200.24; 73/421.5 R
[58] Field of Search ............. 128/2.08, 2 C; 417/234, 417/559; 73/28, 421.5 R, 262, 269; 33/179; 92/92, 94, 98 R, 5 R

[56] References Cited

U.S. PATENT DOCUMENTS

| 3,097,639 | 7/1963 | Streimer | 128/2.08 |
| 3,410,059 | 11/1968 | Garnier | 73/421.5 R |
| 3,483,861 | 12/1969 | Tiep | 128/2.08 |
| 3,802,250 | 4/1974 | Garnier | 73/28 |
| 3,956,940 | 5/1976 | Guild | 73/421.5 R |

FOREIGN PATENT DOCUMENTS

| 673719 | 1/1930 | France | 128/2.08 |
| 1480160 | 4/1967 | France | 128/2.08 |

Primary Examiner—Willis Little
Attorney, Agent, or Firm—David H. Semmes

[57] ABSTRACT

Device for sampling air in proportion to respiration, particularly the collection of air pollutants in proportion to the actual respiration of the wearer. The pump is supported adjacent the thoracic cavity by means of a harness and is activated by the expansion and contraction of the thoracic cavity during respiration, so as to draw air through an air sampling monitor.

15 Claims, 3 Drawing Figures

U.S. Patent
Feb. 12, 1980
4,187,836
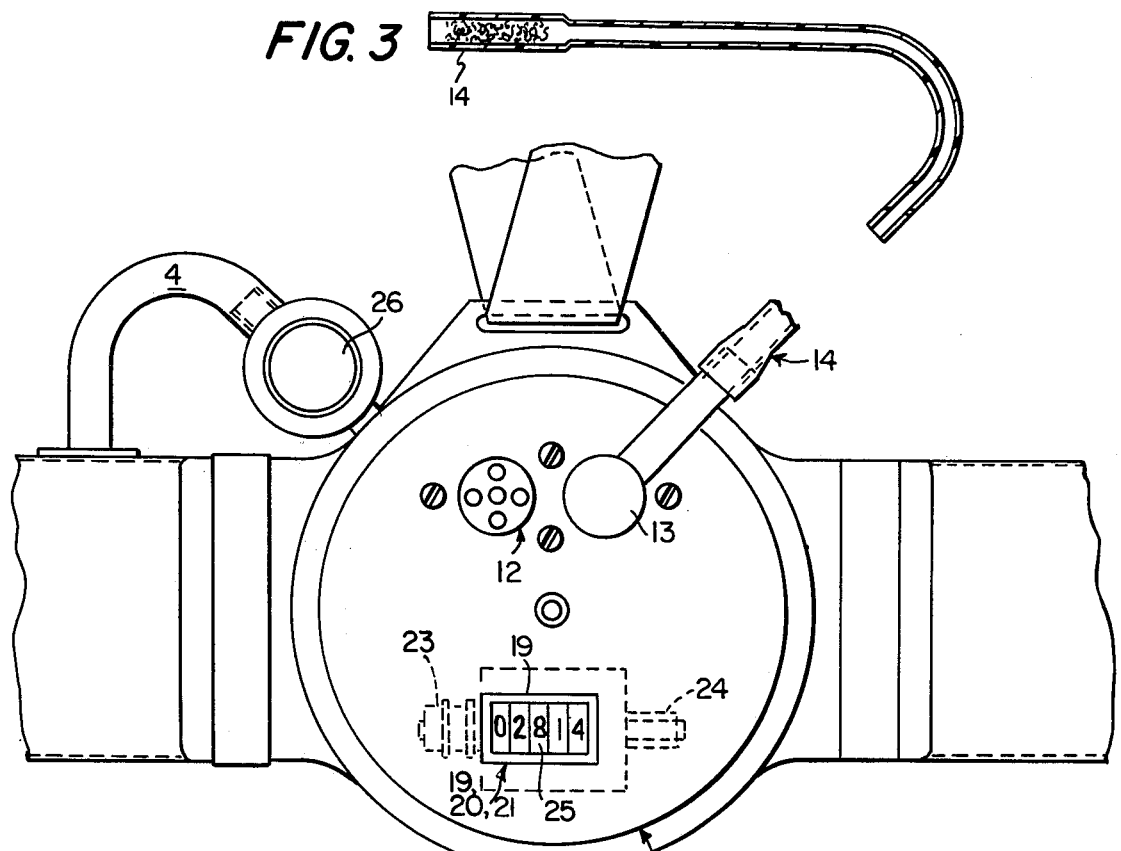
FIG. 3
FIG. 1
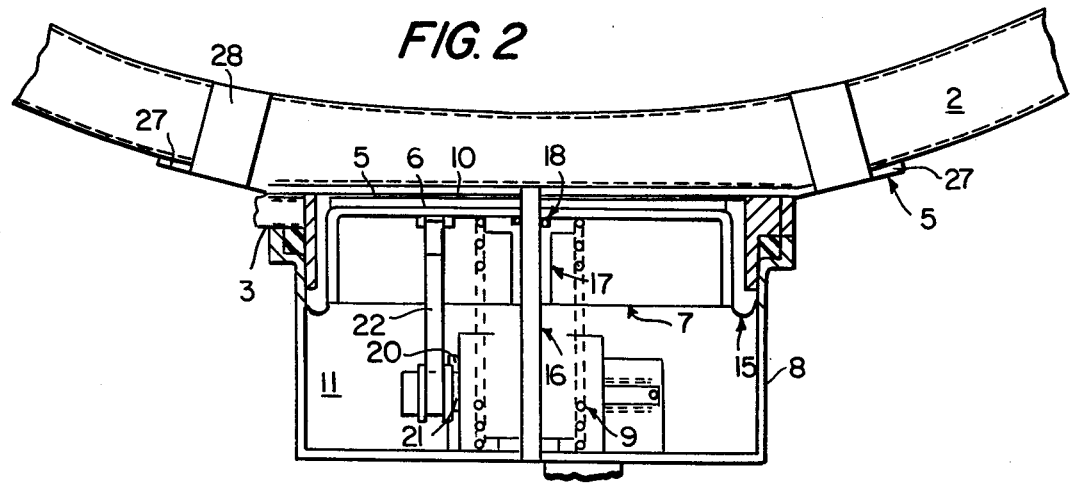
FIG. 2

FLOATING PISTON RESPIRATING PUMP

CROSS REFERENCE TO RELATED APPLICATIONS

A modification and improvement of the respirating pump structure disclosed in Applicants' simultaneously filed METHOD FOR SAMPLING AIR IN PROPORTION TO RESPIRATION (Ser. No. 901,654 filed May 1, 1978). Other copending applications are Ser. No. 901,861 and Ser. No. 901,862, both filed May 1, 1978.

BACKGROUND OF THE INVENTION

1. Field of the Invention:

Although a considerable variety of instrumentation such as impingers, cascade impactors, battery powered air samplers, diffusion collectors and gas-stain detector tubes has been developed for application in monitoring ambient and industrial atmospheres, none may be considered to measure the exposure of an individual to noxious airborne components. All electrically powered and diffusion collection devices fail to measure the varied intake of undesirable gases and particulates which are inhaled into the lungs of an individual, as diverse demands for oxygen are met in response to a range of physiological activities. Thus, exposure to deleterious gases or particulates during periods of high levels of physical activity which result in deep and rapid inspiration are weighed equally in a statistical sense, with periods of shallow breathing in a clean environment by collection devices which sample air in uniform rates. For more accurate correlation with health phenomena it is highly desirable that air sampling for analytical determinations be proportional to the ventilation rate of the individuals under study.

2. Description of the Prior Art:

Being submitted separately under the provisions of 37 C.F.R. 1.97.

SUMMARY OF THE INVENTION

Method for sampling air pollution in proportion to respiration, comprising supporting an air sampling monitor adjacent the mouth of a respirant human, pumping air through the sampler, according as the respirant's thoracic cavity expands and contracts and gauging the amount of pollutants collected within the air sampling monitor as the amount of pollutants actually inhaled by the respirant during a given period. The suggested device includes a floating piston pump with air sampling inlet. The pump is supported adjacent the thoracic cavity and displays the volume of air being pumped in digital readout, as a function of total volume of air being inhaled by the respirant. The total volume of air is correlated with the amount of pollutants collected within the air sampling inlet during the given period.

A modified personal monitor utilizes a foam-filled belt or envelope which is fastened around the torso. Inhalation is accompanied in this device by forcing air under a floating piston which exhausts sampled air from the upper side of a cylindrical pump configuration. Exhalation draws air through a standard sampler tubing into the top of the cylinder.

In this device the expansion and contractions of the torso diameter are sensed by a soft, foam filled belt, or an air inflated belt or pad. This section is fastened at the rear of the torso with an adjustable coupling in order to accomodate various body circumferences. The belt or pad may be supported by a harness which has straps which pass over the shoulders. The harness may also have leg straps or belt connectors for use when motion is sufficiently vigorous to cause displacement of the belt.

The belt is adjusted to fit the wearer during an exhalation. During inhalation when the diameter of the wearer increases, air is forced from the belt into the bottom or inner section of a cylinder housing. As the air enters it forces a floating cylinder which is sealed by a rolling diaphragm to move outwardly. During this movement air is exhausted from the outer section of the cylinder through an exhaust valve. As the piston passes its position of maximum displacement and starts to return to its original position, the pressure differential closes the exhaust valve and opens an intake valve which is connected to the sampling section and its connecting tubing. During the return stroke, air is drawn through the sampling section into the outer portion of the cylinder housing. This action controls sample introduction into the absorbent or particle filter sections. Air flow is controlled by two rubber poppet valves each of which consists of rubber discs sealing against rubber O-rings. These valves are relatively large in area and are closed by weak compression springs. A very small force is required to open each one. The inlet valve is positioned so that it opens when the pressure within the cylinder housing falls below atmospheric. The exhaust valve operates in the opposite fashion; it closes when the internal pressure is lowered.

Movement of the floating piston which is controlled by air pressure from the belt is recorded during its movement toward the base of the cylinder housing. All movements of the piston are transmitted to a digital counter by means of metal tape and a tape pulley positioned upon a counter shaft. A torsion spring is used to assist the return of the tape pulley to its original position. The digital counter, which is operated by the pulley and tape, registers piston movement in one direction, during exhalation. This selectivity is achieved by inclusion of a micro scale clutch and brake on the counter shaft. Thus, the counter is not in motion during the portion of the cycle corresponding to inhalation, when air is forced into the cylinder housing by the respiration of the wearer is directly determinable in terms of the revolution counter reading, multiplied by a fixed calibration factor. A volume of 100 ml of gas is drawn into the sampler for each 1" travel of the piston.

In order to avoid problems associated with slow leakage from the belt envelope or associated fittings, the connection between the belt and the inner section of the cylinder housing contains an equalization valve. The function of this valve is to allow the pressure within the belt volume to equilibrate with atmospheric pressure. Like the intake and exhaust valves in the sampling system it is fabricated of rubber and retained in position by a weak compression spring.

BRIEF DESCRIPTION OF THE DRAWINGS

FIG. 1 is a fragmentary front elevation of a floating piston pump housing secured by an adjustable belt, and supporting both an air sampling tube and a five digit counter display;

FIG. 2 is a fragmentary horizontal section of the pump housing; and

FIG. 3 is a vertical elevation of a conventional air sampling tube, containing in this case silver wool, and attachable to the air inlet in the pump housing.

DESCRIPTION OF THE PREFERRED EMBODIMENTS

A mechanical configuration for the floating piston pump is shown in FIGS. 1 and 2. Belt 1 is comprised of a flexible plastic material which is filled with a porous plastic foam. The foam filled belt forms a sealed envelope 2 which forces air through the inlet 3 to diaphragm 6 through a belt-to-diaphragm tube 4 and equalization valve 26 when the torso of the wearer expands during inhalation. As the air from belt 1 is forced into the expandable zone 10 between base plate 5 and rolling diaphragm 6, the transferred volume forces piston 7 to move axially within the cylinder housing 8. Additional support for cylinder housing 8 may be in the form of shoulder strap 27, shown fragmentarily in FIG. 1. Also, support loops 28 may be provided for securing the housing extensions 27 to the belt. Piston 7 moves outwardly against the pressure supplied by compression spring 9 until the air pressure within the belt envelope 2 and expansion zone 10, as well as the compressive forces of spring 9, are equal. This movement is accomplished by reducing gas volume 11 which is under piston 7. During this outward movement of piston 7, air is ejected through the exhaust valve 12. As wearer inhalation ceases, exhaust valve 12 closes and the inlet valve 13 opens, drawing air through the sample inlet tube 14. Sample inlet tube 14 may be of the type illustrated in FIG. 3, in the form of ¼" I.D. plastic tubing containing a silver wool filling, a 0.5 microporous filter or an inner coating such as sodium bicarbonate. This sampling stroke continues until piston 7 is reseated at the bottom of the cylinder housing 8 with compression spring 9 at full extension.

Piston 7, which draws sample air through sample inlet tube 14, is loosely fitted into cylinder housing 8. No dimensional tolerances are required to obtain the pumping action of piston 7. The rolling diaphragm 15 supercedes all needs for careful fitting of the mechanical parts. Diaphragm 15 may be of the "Bellofram" type, having a one inch stroke upon a volume of 100 cc. of air. However, to keep piston 7 centered within housing 8, piston 7 is moved upon guide rod 16, secured at one end to base plate 5 and at its other end to cylinder housing 8. A guide bushing 17 is fitted into piston 7, so as to engage guide rod 16 and provide reproducible motion in the horizontal plane. Gas leakage between the expandable volume 10 and piston volume 11 is avoided by use of a Teflon O ring seal 18.

For determination of that volume of gas which is drawn into the volume 11 under piston 77, a five digit counter 19 is mounted within cylinder housing 8, so that rotation of the counter in one direction serves as a cumulative indicator of piston 7 travel.

The counter subassembly consists of counter 19 mounted upon shaft 28, an internal clutch 20 and brake 21, a metal tape 22, a tape pulley 23 and a torsion spring 24. As piston 7 moves away from base plate 5 during inhalation, the counter brake 21 is engaged, preventing the counter from rotating. However, clutch 20 is disengaged allowing the tape pulley 23 to rotate to collect metal tape 22. Torsion spring 24 acts to wind the metal tape 22 onto the tape pulley 23. When piston 7 reaches its position of maximum travel away from base plate 5 in each stroke, counter brake 21 releases, the shaft clutch 20 engages and the counter dial 25 rotates, while piston 7 returns to base plate 5. During this action, torsion spring 24 rewinds to its maximum torsion while the compression spring 9 exerts its minimum pressure. Thus, movement of piston 7 is recorded, while an air sample is being drawn through air sample inlet tube 14. By calibration against a dry test meter, the volume equivalent to a one digit change in the counter dial 25 has been determined. For example, for a 2.69 inch (o.d.) piston 7 operating in a 3.0 inch (i.d.) cylinder housing a travel of 1 inch corresponds to drawing a sample of 100 ml of air through the sampling tube. This would give a counter reading change of 10 units. That is, each counter unit is equivalent to 10 cc sample volume in this example.

The vertical display of the pump and counter is shown in the lower portion of FIG. 1. The air inlet tube 4 from belt envelope 2 to the gas space 10 under piston 7 may be provided with an in-line pressure equalization valve 26.

We claim:

1. A floating piston respirating pump device adapted for support upon the thoracic cavity, which comprises in combination:
   (a) a belt defining an enclosed air space, and adapted for support against the thoracic cavity; and,
   (b) a pump housing mounted upon said belt, and including inlet means to allow ambient air to enter, and outlet means to allow ambient air to leave, said housing in response to a pumping action; wherein,
   (c) said pump housing further includes a diaphragm which is movably supported therewithin to define, with an inner end of said housing, a free volume space, which space being communicated with the enclosed air space within said belt; and,
   (d) a piston operably connected to said diaphragm, and movable within said housing upon movement of said diaphragm, to define a pumping chamber with an outer end of said housing, wherein when said free volume space is expanded, said piston defines a minimized pumping volume whereby, the expansion and contraction of the thoracic cavity, during respiration, is operable to actuate said piston within said housing to cause ambient air to enter and leave said housing; and,
   (e) a linear counter means is further mounted within said housing, in operative connection to the piston, so as to count the piston movements within said housing, which movement being a function of respiration of one wearing said device.

2. A respirating pump adapted for support upon the thoracic cavity as in claim 1, including:
   (f) an air pollution sampler affixed to said air inlet, so as to measure ambient air pollutants during respiration.

3. A respirating pump adapted for support upon the thoracic cavity as in claim 2, said belt having a foamed interior communicant with said free volume space adjacent said diaphragm.

4. A respirating pump adapted for support upon the thoracic cavity as in claim 3, said inlet means includes a valve valve including a diaphragm assembly such that air enters into said housing, as said diaphragm is collapsed during exhalation.

5. A respirating pump adapted for support upon the thoracic cavity as in claim 4, said outlet means including a diaphragm such that air is exhausted from said housing upon expansion of said diaphragm during inhalation.

6. A respirating pump adapted for support upon the thoracic cavity as in claim 5, including an equilibrating valve mounted intermediate said diaphragm free volume space and the interior of said belt, so as to equilibrate the pressure of air entering into said free volume space with the volume of air admitted through said air inlet upon movement of said diaphragm.

7. A respirating pump adapted for support upon the thoracic cavity as in claim 6, including a base plate fitted to the inner side of said housing and mountable upon said belt.

8. A respirating pump adapted for support upon the thoracic cavity as in claim 7, said piston being mounted upon an axial guide rod extending from the inner end to the outer end of said housing.

9. A respirating pump adapted for support upon the thoracic cavity as in claim 8, including a compression spring interposed between the outer end of said housing and said piston, so as to urge said piston and diaphragm to collapsed position, as during exhalation.

10. A respirating pump adapted for support upon the thoracic cavity as in claim 9, including:
   (g) a digital display counter mounted in said housing and in contact with said piston, so as to digitally display upon the exterior of said housing accumulated piston movements, as a function of air volume inhaled during a given period.

11. A respirating pump adapted for support upon the thoracic cavity as in claim 10, said housing including at least one shoulder strap aperture, such that said belt may be adjusted vertically with respect to the thoracic cavity.

12. A respirating pump adapted for support upon the thoracic cavity as in claim 11, said counter including a transverse shaft and supporting a helically wound tape connected to said piston.

13. A respirating pump adapted for support upon the thoracic cavity as in claim 12, said counter including a clutch and brake mechanism, such that said counter may be selectively turned on and off.

14. A respirating pump adapted for support upon the thoracic cavity as in claim 13, said counter including a torsion spring urging rotation of said shaft to wind said tape during movement of said piston.

15. A respirating pump adapted for support upon the thoracic cavity as in claim 2, wherein said air pollution sampler is a tube type extending from said air inlet to the mouth area of the respirant.

* * * * *